United States Patent [19]

Snowden et al.

[11] Patent Number: 5,268,355
[45] Date of Patent: Dec. 7, 1993

[54] FURAN ESTERS AND THEIR USE AS PERFUMING INGREDIENTS

[75] Inventors: Roger L. Snowden, Viry, France; Sina D. Escher, Confignon, Switzerland

[73] Assignee: Firmenich S.A., Geneva, Switzerland

[21] Appl. No.: 15,093

[22] Filed: Feb. 9, 1993

[30] Foreign Application Priority Data

Mar. 6, 1992 [CH] Switzerland ............................ 721/92

[51] Int. Cl.$^5$ ................................. A61K 7/46
[52] U.S. Cl. ............................ 512/13; 549/458; 252/174.11; 252/8.6; 424/76.4
[58] Field of Search .................... 512/13; 549/458; 424/76.4; 252/174.11, 8.6

[56] References Cited

U.S. PATENT DOCUMENTS

| | | | |
|---|---|---|---|
| 3,029,255 | 4/1962 | Stoll | 512/13 |
| 3,427,328 | 2/1969 | Sandermann et al. | 512/13 |
| 3,951,825 | 4/1976 | Auger et al. | 512/13 |
| 4,633,011 | 12/1986 | Buchi et al. | 549/458 |

FOREIGN PATENT DOCUMENTS

| | | | |
|---|---|---|---|
| 2-83378 | 3/1990 | Japan | 549/458 |
| 6919189 | 7/1970 | Netherlands | 549/458 |
| 881535 | 11/1961 | United Kingdom | 549/458 |

*Primary Examiner*—James H. Reamer
*Attorney, Agent, or Firm*—Pennie & Edmonds

[57] ABSTRACT

Compounds of formula

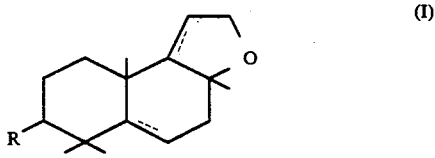

(I)

having a double bond in one of the positions indicated by the dotted lines and wherein symbol R represents a hydrogen atom or a methyl radical, are useful ingredients for the preparation of perfuming compositions and perfumed articles, to which they impart odor notes of the woody-amber type.

10 Claims, No Drawings

FURAN ESTERS AND THEIR USE AS PERFUMING INGREDIENTS

BRIEF SUMMARY OF THE INVENTION

The invention relates to compounds of formula

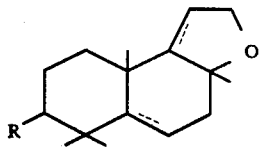

(I)

having a double bond in one of the positions indicated by the dotted lines and wherein symbol R represents a hydrogen atom or a methyl radical.

The invention also has as its object a method to confer, improve, enhance or modify the odor properties of a perfuming composition or a perfumed article, which method comprises adding to said composition or article a fragrance effective amount of a compound of formula (I) as defined above.

According to the invention, there is also provided a perfuming composition or a perfumed article containing as an active perfuming ingredient a compound of formula (I) as defined above.

A further object of the invention is a process for the preparation of a compound of formula

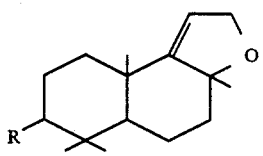

(Id)

wherein symbol R represents a hydrogen atom or a methyl radical, comprising the cyclisation by means of an acidic agent of an allenol of formula

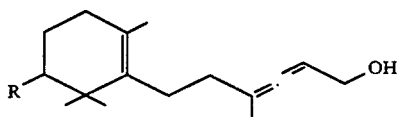

(II)

where R is defined as above.

Novel compounds of formula (II) are also an object of the invention.

THE INVENTION

The compounds of formula (I) defined above are unsaturated analogues of a much appreciated perfuming ingredient, i.e. AMBROX ® (tetramethyl perhydronaphthofuran; origin: Firmenich SA, Geneva, Switzerland). We have now discovered that, in spite of their structure being very close to that of AMBROX ®, compounds (I) possess odor properties which are distinct from those of the latter and that may prove more easily adapted to certain types of perfumery applications.

Compounds (I) possess several chiral centers and, thus, can assume several stereoisomeric forms, racemic or optically active. According to the invention, preferred perfuming ingredients comprise 2,3a,4,5-,5aβ,6,7,8,9,9a-decahydro-3aα,6,6,9aα-tetramethyl-naphtho[2,1-b]furan of formula

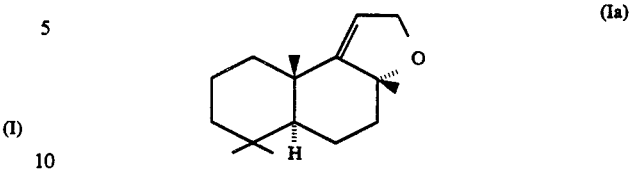

(Ia)

as well as the mixtures containing a preponderant amount of this compound together with minor amounts of any one of its isomers. This compound has been found to possess a woody-amber note, very powerful and with an enhanced woody character relative to that of AMBROX ®. The odor note of compound (Ia) is in fact quite unexpected in that, unlike what is the case with AMBROX ®, it is mainly the top note that possesses a marked amber character. Compound (Ia) is therefore particularly useful for the preparation of perfuming compositions in which it is desired to enhance the impact of the amber note upon application, while keeping the body woody character.

As shown further on, the synthesis of compound (Ia) can lead to mixtures rich in this compound, which also contain minor quantities of one or several of its isomers. Such mixtures have been found to be just as useful for the perfumery applications according to the invention, since they also possessed the desired odor characters. Consequently, when, in the examples, reference is made to compound (Ia), it is implied that one is also referring to said mixtures.

Another preferred compound of the invention is (−)-(3aR)-1,2,3a,4,6,7,8,9,9a,9bβ-decahydro-3aα,6,6,9aα-tetramethylnaphtho[2,1-b]furan of formula

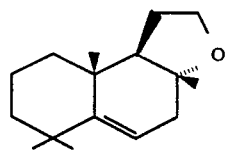

(Ib)

This compound develops a very powerful woody-amber fragrance, with a woodier and less amber-animal character than that of AMBROX ®, a note that also turns out to be more tenaceous than that of AMBROX ®, particularly on cloth.

2,3a,4,5,5aβ,6,7,8,9,9a-Decahydro-3aα,6,6,7α,9aα-pentamethylnaphtho[2,1-b]furan of formula

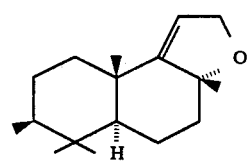

(Ic)

is also a preferred perfuming ingredient according to the invention, possessing a woody-amber note with similar characteristics, but more powerful than that of its unmethylated homolog (Ia). Its note is also less amber, and particularly less animal and marine-like than that of AMBROX ®.

As a result of their olfactive qualities, the compounds according to the invention are convenient for applications both in fine and technical perfumery. They can be advantageously used for the preparation of perfuming bases and compositions, perfumes and colognes, but they are also very convenient for perfuming various articles such as soaps, bath and shower gels, shampoos and hair conditioners, air or body deodorants, as well as cosmetic preparations. Their use for perfuming detergents and fabric softeners, or yet household products is also advantageous.

In the above-mentioned applications, compounds (I) can be used alone or, as is more usual in perfumery, in admixture with current perfuming ingredients, solvents or adjuvants. A detailed description of such coingredients is quite superfluous as the man in the art is capable of choosing them as a function of the desired odor effect and can resort to textbooks such as that of S. Arctander, Perfume and Flavor Chemicals, Montclair, N.J., USA (1976). The desired odor effect also determines the choice of the concentrations in which the compounds of the invention can be used for the above-mentioned applications, concentrations which also depend on the nature of the other ingredients present in a given composition.

Although these concentrations can thus vary in a wide range of values, one can cite, by way of example, concentration values of the order of 0.5 to 5%, or even 10% or more by weight, relative to the weight of the composition into which compounds (I) are incorporated. Much lower proportions of these compounds will generally be used when they are employed for perfuming the various articles cited above.

The compounds according to the invention formula

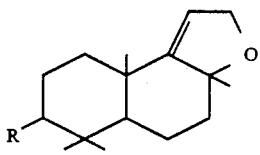

(Id)

wherein symbol R stands for a hydrogen atom or a methyl radical, are prepared via or original process comprising the cyclisation, by means of an acidic agent, of an allenol of formula

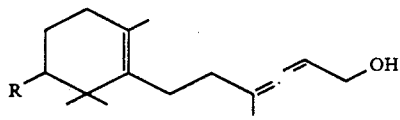

(II)

wherein R has the meaning indicated above.

Allenols (II) are novel compounds according to the invention which can be prepared starting from β-dihydroionone and β-dihydroirone, as is described in detail in the following preparation examples.

The invention will also be described in further detail by way of examples of perfumery applications.

EXAMPLE 1

Preparation of 2,3a,4,5,5aβ,6,7,8,9,9a-decahydro-3aα,6,6,9aα-tetramethylnaphtho[2,1-b]furan a) A mixture of 4-(2,6,6-trimethyl-1-cyclohexen-1-yl)-2-butanone (107 g, 0.55 mol) and propargyl alcohol (34 g, 0.61 mol) was added dropwise during 1.5 h to a mechanically stirred slurry of powered KOH (Fluka, 230 g, 4.1 mol) in THF (tetrahydrofuran 800 ml) maintained at 20° C. After a further 3 h, the brown mixture was poured into a cold solution of NH$_4$Cl (250 g, 4.7 mol) in H$_2$O (800 ml) and the phases separated. Extraction of the aqueous phase with ether and concentration of the combined organic phase afforded a reddish brown solid which was recrystallized from petroleum ether (80/100) to furnish 4-methyl-6-(2,6,6-trimethyl-1-cyclohexen-1-yl)-2-hexyn-1,4-diol as a pale yellow powder (110 g, 80% yield).

M. p. 83°–84° C.

R$_f$(cyclohexane/ethyl acetate 1:1) 0.32.

IR(CHCl$_3$): 3550, 3350 (broad), 2900, 2840, 1440, 1360, 1344, 1082, 1040, 980 cm$^{-1}$.

NMR($^1$H, 360 MHz, D$_2$O): 1.00(s, 6H), 1.41(s, 3H); 1.50(2H); 1.57(2H); 1.61(s,3H); 1.73(2H); 1.90(broad t, J=7 Hz, 2H); 2.19(2H); 4.30(s, 2H) δ ppm.

NMR($^{13}$C): 136.3(s); 127.5(s); 89.5(s); 81.7(s); 68.3(s); 50.7(t); 43.5(t); 39.9(t); 35.2(s); 32.8(t); 29.3(q); 28.7(q); 23.6(t); 19.8(q); 19.6(t) δ ppm.

MS: 250(0, M+), 232(9), 217(19), 161(37), 145(40), 133(40), 121(100), 105(79), 95(87), 81(80).

b) Triethylamine (12 g, 0.12 mol) was added dropwise to a mixture of the diol prepared in a) (25 g, 0.1 mol) and acetic anhydride (12 g, 0.12 mol) at r.t. (exothermic reaction: T°→58°). After a further 15 min, the cooled mixture was poured into cold 10% aqueous HCl and extracted with ether (3×100 ml). Workup and distillation i.v. afforded 4-hydroxy-4-methyl-6-(2,6,6-trimethyl-1-cyclohexen-1-yl)-2-hexynyl acetate as a colorless syrup (28.3 g, 97% yield).

B. p. 144°–150° C. (bath temperature)/7 Pa.

R$_f$(cyclohexane/ethyl acetate 7:3) 0.41.

IR(CHCl$_3$): 3540, 3380 (broad), 2900, 2850, 1722, 1440, 1368. 1350, 1220, 1100, 958 cm$^{-1}$.

NMR($^1$H, 360 MHz, D$_2$O): 100(s, 6H); 1.41(2H); 1.49(s, 3H); 1.56(2H); 1.60(S, 3H); 1.73(2H); 1.90(broad t, J=7 Hz, 2H); 2.09(s, 3H); 2.19(2H); 4.71(s, 2H) δ ppm.

MS: 292(0, M+), 274(8), 217(31), 199(27), 161(36), 143(44), 121(100), 105(71), 95(94), 81(76).

c) A solution of 3,4-dihydro-2H-pyran (15 g, 0.17 mol) in diethyl ether (40 mol) was added dropwise during 20 min in a stirred solution of the acetate prepared in b) (15 g, 0.051 mol) in diethyl ether (70 ml) containing p-toluenesulfonic acid (0.75 g, 4 mmol) at 25° C. After a further 30 min, the mixture was washed successively with saturated aqueous NaHCO$_3$ solution and H$_2$O. Workup and distillation i.v. afforded 4-(tetrahydro-2(2H)-pyranyloxy)-4-methyl-6-(2,6,6-trimethyl-1-cyclohexen-1-yl)-2-hexynyl acetate as a colorless oil (GC purity: 91%) (19 g, 89% yield).

B. p. 147°–157° C./7 Pa.

R$_f$(cyclohexane/ethyl acetate 7:3) 0.52.

IR: 2940, 2870, 1720, 1430, 1360, 1350, 1220, 1108, 1020, 960, 860 cm$^{-1}$.

NMR(1H, 360 MHz, D$_2$O): 1.00(s, 6H), 1.41(2H); 1.47 and 1.52(2s, 3H); 1.61(s, 3H); 145–1.90(10H); 1.89(broad t, J=7 Hz, 2H); 2.09 and 2.10(2s, 3H); 2.18(2H); 3.51(1H); 3.93 and 3.98(2m, 1H); 4.72 and 4.73(2s, 2H); 5.00 and 5.08(2m, 1H) δ ppm.

MS major isomer: 376(0, M+), 199(9), 137(31), 121(16), 105(11), 95(31), 85(100), 81(27).

MS minor isomer: 376(0, M+), 199(21), 137(36), 121(35), 105(24), 95(59), 85(100), 81(42).

d) A solution of the acetate prepared in c) (15 g, 0.036 mmol) in THF (120 ml) was added dropwise during 45 min to a stirred slurry of LiAlH$_4$ (2.08 g, 0.055 mol) in THF (140 ml) at reflux under $N_2$. After a further 10 min at reflux, the cooled mixture was treated successively with $H_2O$ (2 ml), 20% aqueous NaOH (2 ml) and $H_2O$ (12 ml). Filtration (Hyflo), concentration and distillation i.v. afforded two major fractions: fraction 1 (5.1 g; b.p. 60°–73° C./6.7 Pa) provided, after column chromatography [silica gel (160 g); toluene/ethyl acetate 9:1, followed by $CH_3OH$], 0.91 g (yield 11%) of 4-methyl-6-(2,6,6-trimethyl-1-cyclohexen-1-yl)-2,3-hexadien-1-ol and fraction 2 (7.4 g; b.p. 100°–108° C./6.7 Pa) provided, after column chromatography [silica gel (360 g); toluene/ethyl acetate 9:1], 5.5 g (yield: 65%) of this same compound, in the form of a colorless oil.

B. p. (bulb-to-bulb distillation) 150°–180° C. (bath temperature)/7 Pa.

$R_f$(cyclohexane/ethyl acetate 7:3) 0,41.

IR($CHCl_3$): 3560, 3400 (broad), 2920, 2850, 1944, 1460, 1370, 1358, 1108, 1072, 990 $cm^{-1}$.

NMR($^1H$, 360 MHz, $D_2O$): 0.98(s, 6H); 1.41(2H); 1.56 (2H); 1.58(s, 3H); 1.74(d, J=3 Hz, 3H); 1.90(broad t, J=7 Hz, 2H); 1.99(2H); 2.08(2H); 4.08(d, J=5 Hz, 2H) ; 5.30(m, 1H) δ ppm.

NMR($^{13}C$): 200.0(s); 137.0(s); 127.4(s); 103.6(s); 91.6(d); 61.1(t); 39.9(t); 35.0(s); 34.4(t); 32.8(t); 28.6(2q); 27.1(t); 19.8(q); 19.6(t); 19.2(q) δ ppm.

MS: 234(2, $M^+$), 219(5), 145(36), 133(29), 121(39), 107(46), 95(100), 81(70).

e) A solution of 4-methyl-6-(2,6,6-trimethyl-1-1-cyclohexen-1-yl)-2,3-hexadien-1-ol [obtained in d]; 11 g, 0.044 mol) in $CH_2Cl_2$ (30 ml) was added dropwise during 1 h to a mechanically stirred slurry of 95% aqueous $H_2SO_4$ (11 g, 0.11 mol) in $CH_2Cl_2$ (110 ml) at $-40°$ C. under $N_2$. The dark-red mixture was stirred for a further 3 h at $-40°$ and then poured slowly into a cold solution of $NaHCO_3$ (20 g) in $H_2O$ (250 ml) which was stirred during 30 min at r.t. The resulting white emulsion was partially concentrated (30° C./20×$10^2$ Pa) and the residue was extracted with ether. Workup gave a viscous orange oil (11.2 g) which was distilled i.v. to afford a colorless oil (6.5 g, 64% yield).

B. p. 85°–100° C./6.7 Pa.

GC analysis indicated the presence of four compounds (elution order: Carbowax), $R_f$ 0.18 (toluene), the analytical data of which were the following:

2,3a,4,5,5aα,6,7,8,9,9a-decahydro-3aα,6,6,9aβ-tetramethylnaphtho[2,1-b]furan (5% by weight)

NMR($^1H$, 360 MHz): 0.88(s, 3H); 0.91(s, 3H); 1.13(s, 3H); 1.38(s,3H); 1.00–2.20(11H); 4.37(dd, J=13, 3 Hz, 1H); 4.58(d, J=13, 1.5 Hz, 1H); 5.45(broad s, 1H) δ ppm.

NMR($^{13}C$): 159.4(s); 116.6(d); 86.4(s); 71.8(t); 45.3(d); 42.3(t); 40.3(t); 37.6(s); 33.5(q); 33.3(t); 26.7(q); 26.0(q); 21.4(q); 19.4(t); 17.7(t) (1s not observed) δ ppm.

MS: 234(12, $M^+$), 219(100), 149(17), 123(17), 110(31), 97(69), 81(49), 69(32).

2,3a,4,5,5aα,6,7,8,9,9a-decahydro-3aα,6,6,9aα-tetramethylnaphtho[2,1-b]furan (22% by weight)

NMR($^1H$, 360 MHz): 0.93(s, 3H); 0.94(s, 3H); 1.15(s, 3H); 1.42(s, 3H); 1.00–2.00(11H); 4.47(dd, J=13, 3 Hz, 1H); 4.56(d, J=13, 1.5 Hz, 1H); 5.42(broad s, 1H) δ ppm.

NMR(13C): 150.7(s); 116.6(d); 86.6(s); 71.5(t); 50.5(d); 44.2(t); 39.9(t); 37.2(s); 37.0(t); 34.8(s); 33.1(q); 32.1(q); 28.1(q); 26.1(q); 20.3(t); 19.0(t) δ ppm.

MS: 234(7, $M^+$), 219(65), 110(70), 97(100), 81(58), 69(30).

2,3a,4,5,5aβ,6,7,8,9,9a-decahydro-3aα,6,6,9aα-tetramethylnaphthlo[2,1-b]furan (68% by weight)

IR($CDCl_3$): 2950,1460, 1380, 1140, 1100, 1060, 1020 $cm^{-1}$.

NMR($^1H$, 360 MHz): 0.86(s, 3H); 0.87(s, 3H); 0.94(dd, J=13, 3.5 Hz, 1H); 1.08(s, 3H); 1.16(m, 1H); 1.38(s, 3H); 1.35–1.80(8H); 2.00(dt, J=13, 3.5 Hz, 1H); 4.47(dd, J=13, 3.5 Hz, 1H); 4.58(dd, J=13, 1.5 Hz, 1H); 5.23(broad s, 1H) δ ppm.

NMR($^{13}C$): 156.5(s); 113.1(d); 87.2(s); 72.1(t); 55.3(d); 42.2(t); 42.1(t); 38.1(t); 37.7(s); 33.6(s); 33.4(q); 26.4(q); 21.5(q); 20.3(t0; 19.9(q); 18.6(t); δ ppm.

MS: 234(19, $M^+$), 219(100), 191(32), 110(36), 97(66), 81(51), 69(37).

2,3a,4,5,5aβ,6,7,8,9,9a-decahydro-3aα,6,6,9aβ-tetramethylnaphtho[2,1-b]furan (3% by weight)

MS: 234(8, $M^+$), 219(40), 149(11), 110(58), 97(100), 81(32).

The conditions of the acidic cyclisation of the dienol described above under e) are standard conditions which, in other experiments, were modified in a known way [see, for example, EP-A2-403 945, hereby included by reference] to obtain mixtures which were enriched in 2,3a,4,5,5aβ,6,7,8,9,9a-decahydro-3aα,6,6,9a-tetramethylnaphtho[2,1-b]furan, or even to obtain this compound in its pure form (93% pure).

All the above-mentioned mixtures possessed the desired olfactive qualities of the pure compound, already described in the introduction.

EXAMPLE 2

Preparation of 2,3a,4,5,5aβ,6,7,8,9,9a-decahydro-3aα,6,6,7α,9aα-pentamethylnaphtho[2,1-b]furan a) A mixture of 4-(2,5,6,6-tetramethyl-1-cyclohexen-1-yl)-2-butanone (13 g, 0.061 mol) and propargylic alcohol (4 g, 0.071 mol) was added within 100 min to a mechanically stirred slurry of powdered KOH (26 g, 0.46 mol) in THF (100 ml) at 20° C. under $N_2$. After 3 h at 20°, the brown mixture was poured into a cold solution of $NH_4Cl$ (28 g) in $H_2O$ (100 ml). Extraction with ether, workup and chromatography [$SiO_2$, (200 g), cyclohexane/ethyl acetate 7:3] afforded 4-methyl-6-(2,5,6,6-tetramethyl-1-cyclohexen-1-yl)-2-hexyn-1,4-diol as a viscous pale-yellow oil (12.3 g, 77%).

B.p. (bulb-to-bulb) 180°–200° C./67 Pa.

$R_f$(cyclohexane/ethyl acetate 7:3) 0.14.

IR($CHCl_3$): 3620, 3388 (broad), 3019, 2970, 1374, 1215, 1056, 932 $cm^{-1}$.

NMR($^1H$, 360 MHz, $D_2O$): 0.85(s, 3H); 0.87(d, J=7 Hz, 3H); 1.02(2s, 3H); 1.25–2.05(7H); 1.50(s, 3H); 1.62(s, 3H); 2.20(m, 2H); 4.30(s, 2H) δ ppm.

NMR($^{13}C$): 136.4(s); 127.2(s); 89.5(s); 81.7(s); 68.3(s); 50.7(t); 43.5(t); 39.4(d); 38.4(s); 31.7(t); 29.3(q); 27.3(t); 27.1(q); 23.9(t); 21.8(q); 19.9(q); 16.7(q) δ ppm.

MS: 264(0, $M^+$), 246(3), 231(11), 145(34), 135(82), 121(57), 107(66), 95(78), 43(100).

b) A mixture of the diol prepared in a) (6 g, 0.022 mol), acetic anhydride (2.8 g, 0.027 mol) and triethylamine (2.8 g, 0.028 mol) was stirred at 60° C. during 30 min under $N_2$. The cooled mixture was poured into cold 10% aqueous HCl and extracted with ether. Workup and distillation i.v. afforded 4-hydroxy-4-methyl-6-(2,5,6,6-tetramethyl-1-cyclohexen-1-yl)-2-hexynyl acetate as a viscous pale-yellow oil (6.8 g, 98%).

B.p. 145°-148° C./7 Pa.

R$_f$(cyclohexane/ethyl acetate 7:3) 0.38.

IR(CHCl$_3$): 3599, 3480 (broad), 3019, 2970, 1737, 1434, 1377, 1216, 1027, 965 cm$^{-1}$.

NMR($^1$H, 360 MHz, D$_2$O): 0.84(s, 3H); 0.88(d, J=7 Hz, 3H); 1.02(s, 3H); 1.25-2.30(9H); 1.50(s, 3H); 1.62(s, 3H); 2.10(s, 3H); 4.72(s, 2H) δ ppm.

NMR($^{13}$C): 170.3(s); 136.3(s); 127.2(s); 90.6(s); 77.3(s); 68.2(s); 52.3(t); 43.5(t); 39.4(d); 38.4(s); 31.7(t); 29.3(q); 27.3(t); 27.0(q); 23.9(t); 21.8(q); 20.7(q); 19.9(q); 16.6(q) δ ppm.

MS: 306(0, M$^+$), 288(1), 231(8), 213(9), 175(20), 157(20), 145(23), 135(58), 121(52), 107(40), 95(45), 43(100).

c) A solution of ethyl vinyl ether (2.3 g, 0.032 mol) in toluene (4 ml) was added dropwise within 5 min to a stirred solution of the acetate prepared in b) (6.4 g, 0.021 mol) in toluene (25 ml) containing p-toluenesulfonic acid (50 mg, 2.6 mmol) at −20° C. under N$_2$. After 1 h, this solution was added within 20 min to a stirred slurry of LiAlH$_4$ (1.6 g, 0.042 mol) in THF (80 ml) at 20° C. under N$_2$. After 30 min, H$_2$O (1.6 ml), 20% aqueous NaOH solution (1.6 ml) and H$_2$O (8 ml) were successively added dropwise and the mixture was filtered (Hyflo). Concentration i.v. of the filtrate and chromatography [SiO$_2$ (150 g) toluene/ethyl acetate 9:1, then ethyl acetate) afforded 4-methyl-6-(2,5,6,6-tetramethyl-1-cyclohexen-1-yl)-2,3-hexadien-1-ol as a viscous colorless oil (3.42 g, 66%).

B.p. 108°-114° C./7 Pa.

R$_f$(toluene/ethyl acetate 9:1) 0.32.

IR(CHCl$_3$): 3612, 3480 (broad), 3018, 2970, 1373, 1215, 1008 cm$^{-1}$.

NMR($^1$H, 360 MHz, D$_2$O): 0.83(s, 3H); 0.88(d, J=7 Hz, 3H); 1.00(s, 3H); 1.25-1.60(3H); 1.59(s, 3H); 1.75(d, J=3 Hz, 3H); 1.65-2.20(6H); 4.09(d, J=7 Hz, 2H); 5.31(m, 1H) δ ppm.

NMR($^{13}$C): 200.0(s); 137.1(s); 127.1(s); 103.5(s); 91.6(d); 61.2(t); 39.4(d); 38.2(s); 34.5(t); 31.7(t); 27.3(t); 27.0(q); 21.8(q); 19.2(q); 19.2(q); 16.7(q) δ ppm.

MS: 248(0, M$^+$), 147(30), 133(39), 121(55), 109(57), 95(100), 81(48), 67(57).

d) A solution of the hexadienol prepared in c) (1.6 g, 6.3 mmol) in 2-nitropropane (8 ml) was added dropwise within 15 min to a stirred slurry of FSO$_3$H (1 ml, 0.017 mol) in 2-nitropropane (10 ml) at −90° C. After 15 min, the dark violet mixture was allowed to attain −30° C. and poured into a cold solution of NaHCO$_3$ (6 g) in H$_2$O (50 ml). Extraction with ether, workup and bulb-to-bulb distillation i.v. afforded a semicrystalline pale-yellow oil (1.2 g). Repeated low temperature recrystallisation (petroleum ether 30/50, −70° C.) afforded 2,3a,4,5-,5aβ,6,7,8,9,9a-decahydro-3aα,6,6,7α,9aα-pentamethyl-naphtho[2,1-b]furan as white crystals (0.79 g, 50%).

M.p. 86°-88° C.

R$_f$(toluene/ethyl acetate 19:1) 0.33.

IR(CHCl$_3$): 2971, 1456, 1378, 1215, 1136, 1056, 1014, 855 cm$^{-1}$.

NMR($^1$H, 360 MHz): 0.70(s, 3H); 0.85(d, J=7 Hz, 3H); 0.89(s, 3H); 0.89(s, 3H); 0.92(m, 1H); 1.06(s, 3H); 1.20(m, 1H); 1.30-1.60(5H); 1.39(s, 3H); 1.68-1.78(2H); 2.00(m, 1H); 4.47(dd, J=11.5, 3 Hz, 1H); 4.58(d, J=11.5 Hz); 5.23(broad s, 1H) δ ppm.

NMR($^{13}$C): 156.6(s); 113.3(d); 87.0(s); 72.0(s); 56.1(d); 42.6(d); 42.0(t); 37.9(t); 36.8(s); 29.3(q); 27.4(t); 26.3(q); 20.4(t); 19.8(q); 16.5(q); 16.3(q) δ ppm.

MS: 248(12, M$^+$), 233(58), 163(11), 149(43), 97(100).

EXAMPLE 3

Preparation of (−)-(3aR)-1,2,3a,4,6,7,8,9,9bβ-decahydro-3aα,6,6,9aα-tetramethyl-naphtho[2,1-b]furan a) A solution of (−)-(3aS)-1,2,3a,4,5,5aβ,6,7,8,9,9a,9bβ-dodecahydro-3aα,6,6,9aα-tetramethylnaphtho[2,1-b]furan-4-one ([α]$^{22}_D$=−149°; c=0.877, CHCl$_3$; 3.94 g, 15.8 mmol) in chloroform (80 ml) was treated dropwise with a 0.5M solution of bromine (35 ml, 1.1 eq) in chloroform. The mixture was stirred at RT overnight when TLC indicated practically complete disappearance of the starting furanone. 300 Ml of ether were added and the whole was washed with 10% aqueous NaHSO$_3$-solution. Usual workup gave 5.5 g of crude, crystalline α-bromo ketone. This was heated under argon in DMF (dimethylformamide, Fluka puriss., 95 ml) in the presence of Li$_2$CO$_3$ (5.82 g, 78.8 mmol) and LiBr (5.48 g, 63 mmol) at 100° C. overnight. After workup with ether, 4.05 g of crystalline enone were isolated. Two recrystallizations from hexane afforded 2.22 g (57%) of >99% pure (−)-(3aS)-1,2,3a,4,6,7,8,9,9a,9bβ-decahydro-3aα,6,6,9aα-tetramethylnaphtho[2,1-b]furan-4-one.

M.p. 139°-140° C.

[α]$^{20}_D$=−166.9° (c=0.85, CHCl$_3$).

IR(CHCl$_3$): 1700, 1600, 1240, 1160, 1120, 1060 cm$^{-1}$.

UV(C$_2$H$_5$OH): =$_{max}$=238 nm, ε=12,000.

NMR($^1$H, 360 MHz, CDCl$_3$): 1.17(s, 3H); 1.23(s, 3H); 1.24(s, 3H); 1.33(s, 3H); 3.89(dxdxd, J=8,8,8 Hz, 1H); 4.07(dxdxd, J=8,8,3, 1H); 5.92(s, 1H) δ ppm.

MS: 248(2, M$^+$), 233(4), 164(100), 149(43), 108(21), 93(12), 43(19).

The starting furanone can be obtained as described by M. Gonzalez-Sierra et al., Heterocycles, 26, 2801 (1987).

b) A mixture of the enone prepared in a) (1200 mg, 4.8 mmol), hydrazine hydrate (1200 mg) and anhydrous ethanol (24 ml) was refluxed under argon for 24 h. It was concentrated at reduced pressure and azeotroped twice with benzene. The crude hydrazone was dissolved in distilled diethylene glycol and 840 mg of powdered potassium hydroxide were added. The whole was heated at 190° C. whereby the volatiles were allowed to distill off. When the hydrazone had disappeared (30 min), the mixture was cooled and extracted into pentane-ether 1:1. After usual workup, the residue was distilled evaporatively at 110°-20° C./10$^3$ Pa to give 870 mg of the desired product 85% pure. MPLC on silica gel (Lobar B) with hexane-ether 95:5 afforded 650 mg (57%) of >98% pure (−)-(3aR)-1,2,3a,4,6,7,8,9,9a,9bβ-decahydro-3aα,6,6,9aα-tetramethylnaphtho[2,1-b]furan which was recrystallized from hexane to provide an analytical sample >99% pure.

M.p. 60.5°-61.5° C.

[α]$^{20}_D$=−96.1° (c=1.00, CHCl$_3$).

Threshold value.: 0.17 ppb.

NMR($^1$H, 360 MHz): 1.06(s, 3H); 1.08(s, 3H); 1.12(s, 3H); 1.13(s, 3H); 2.24(d, J=4 Hz, 2H); 3.85(dxdxd, J=8, 8, 8 Hz, 1H); 3.98(dxdxd, J=8, 8, 4 Hz, 1H); 5.36(t, J=4 Hz, 1H) δ ppm.

MS: 234(4, M$^+$), 219(11), 150(58), 135(84), 84(100), 43(68).

EXAMPLE 4

Perfuming composition

A base perfuming composition intended for a body deodorant was prepared by admixing the following ingredients:

| Ingredients | Parts by Weight |
| --- | --- |
| Benzyl acetate | 60 |
| Geranyl acetate | 30 |
| Linalyl acetate | 250 |
| 10% *Methyl nonyl aldehyde | 125 |
| Allyl amyl glycolate | 125 |
| Astrotone ®[1] | 250 |
| Pure citral | 60 |
| Lemon essential oil | 370 |
| Citronellol | 60 |
| Coumarin | 370 |
| Dihydromyrcenol ®[2] | 870 |
| Estragol | 370 |
| Eugenol | 60 |
| 10% *Isobutylquinoleïne[3] | 60 |
| Lavandin oil | 1860 |
| Lilial ®[4] | 430 |
| Lyral ®[5] | 100 |
| Crystalmoss | 155 |
| Hedione ®[6] | 400 |
| Patchouli essential oil | 745 |
| Phenethylol | 60 |
| Amyl salicylate | 430 |
| Benzyl salicylate | 1230 |
| Sandela ®[7] | 750 |
| Ylang essential oil | 155 |
| Vertofix coeur[8] | 370 |
| 10% *2,4-Dimethyl-3-cyclohexene-1-carbaldehyde[9] | 155 |
| Total | 9900 |

*in dipropylene glycol
[1] origin: Rhone-Poulenc.
[2] 2,6-dimethyl-7-octen-2-ol; origin: International Flavors % Fragrances Inc., U.S.A.
[3] 6-(1-methylpropyl)quinolein; origin: International Flavors % Fragrances Inc., U.S.A.
[4] 3-(4-tert-butyl-1-phenyl)-2-methylpropanal; origin: Givaudan-Roure, Vernier, Switzerland.
[5] 4-(4-hydroxy-4-methylpentyl)-3-cyclohexene-1-carboxaldehyde; origin: International Flavors % Fragrances Inc., U.S.A.
[6] methyl dihydrojasmonate; origin: Firmenich SA, Geneva, Switzerland.
[7] 3-(isocamphyl-5)-cyclohexan-1-ol (isomer mixture); origin: Givaudan-Roure, Vernier, Switzerland.
[8] origin: International Flavors & Fragrances Inc., U.S.A.
[9] origin: Firmenich SA, Geneva, Switzerland.

To 99 parts by weight of this amber, herbaceous, floral type base composition, there was separately added 1 part by weight of AMBROX ® DL to obtain a composition A, 1 part by weight of 2,3a,4,5,5aβ,6,7,8,9,9a-decahydro-3aα,6,6,9aα-tetramethylnaphtho[2,1-b]furan to obtain a novel composition B and 1 part by weight of (−)-(3aR)-1,2,3a,4,6,7,8,9,9a,9bβ-decahydro-3aα,6,6,9aα-tetramethylnaphtho[2,1-b]furan to obtain a novel composition C.

These three compositions were then submitted to a blind evaluation by a panel of 9 expert perfumers.

According to this panel, novel composition B possessed an odor whose top amber note was exhalted relative to that of composition A. Composition B has less body than the latter, but its odor note possessed a more marked woody character than that of the fragrance of composition A.

On the other hand, the odor of composition C had less amber character than that of composition A, but a much enhanced woody character and, in particular, was remarkably more tenaceous on the skin than that of composition A.

What is claimed is:

1. A compound of formula

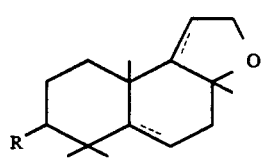

(I)

having a double bond in one of the positions indicated by the dotted lines and wherein symbol R represents a hydrogen atom or a methyl radical.

2. 2,3a,4,5,5aβ,6,7,8,9,9a-Decahydro-3aα,6,6,9aα-tetramethylnaphtho[2,1-b]furan or any mixture containing a preponderant amount of the former together with minor amounts of any of its isomers.

3. (−)-(3aR)-1,2,3a,4,6,7,8,9,9a,9bβ-Decahydro-3aα,6,6,9aα-tetramethylnaphtho[2,1-b]furan.

4. 2,3a,4,5,5aβ,6,7,8,9,9a-Decahydro-3aα,6,6,7α,9aα-pentamethylnaphtho[2,1-b]furan.

5. A method to confer, improve, enhance or modify the odor properties of a perfuming composition or a perfumed article, which method comprises adding to said composition or article a fragrance effective amount of a compound of formula (I) as defined in claim 1.

6. A perfuming composition or a perfumed article containing as an active perfuming ingredient a compound of formula (I) as defined in claim 1.

7. A perfuming composition or a perfumed article according to claim 6, wherein said active perfuming ingredient is chosen from the ground consisting of:
 a) 2,3a,4,5,5aβ,6,7,8,9,9a-decahydro-3aα,6,6,9aα-tetramethylnaphtho[2,1-b]furan or any mixture containing a preponderant amount of the former together with minor amounts of any of its isomers
 b) (−)-(3aR)-1,2,3a,4,6,7,8,9,9a,9bβ-decahydro-3aα,6,6,9aα-tetramethylnaphtho[2,1-b]furan
 c) 2,3a,4,5,5aβ,6,7,8,9,9a-decahydro-3aα,6,6,7α,9aα-pentamethylnaphtho[2,1-b]furan.

8. A perfumed article according to claim 6 selected from the group consisting of a perfume, a Cologne, a soap, a shampoo, a hair conditioner, a bath or shower gel, a body or air deodorant, a cosmetic preparation, a detergent, a fabric softener and a household product.

9. The method of claim 5 which further comprises adding to said perfuming composition or perfumed article from about 0.5 to about 10% by weight of said compound of formula (I).

10. A perfumed article according to claim 6 wherein said compound of formula (I) is present in an amount of between about 0.5 and 10% by weight.

* * * * *